United States Patent [19]

Protiva et al.

[11] Patent Number: 4,678,788
[45] Date of Patent: Jul. 7, 1987

[54] N-SUBSTITUTED 2-CHLORO-7-FLUORO-10-PIPERAZINO-10,11-DIHYDRODIBENZO (B,F) THIEPINS AND ACID ADDITION SALTS THEREOF

[75] Inventors: Miroslav Protiva; Jiri Jilek; Irena Cervena; Antonin Dlabac; Martin Valchar; Josef Pomykacek, all of Prague, Czechoslovakia

[73] Assignee: Spofa, Spojene Podniky Pro Zdravotnickou Vyrobu, Prague, Czechoslovakia

[21] Appl. No.: 821,992

[22] Filed: Jan. 24, 1986

[30] Foreign Application Priority Data

Jan. 24, 1985 [CS] Czechoslovakia ............... 516-85

[51] Int. Cl.⁴ .................. A61K 31/495; C07D 409/04
[52] U.S. Cl. ................................... 514/254; 544/375; 549/12
[58] Field of Search .................... 544/375; 514/254

[56] References Cited

U.S. PATENT DOCUMENTS 4,144,337  3/1979  Bastian .......................... 544/375
4,243,805  1/1981  Protiva et al. ................. 544/375

Primary Examiner—Glennon H. Hollrah
Assistant Examiner—James H. Turnipseed

[57] ABSTRACT

N-substituted 2-chloro-7-fluoro-10-piperazino-10,11-dihydrodibenzo(b,f)thiepins are disclosed of the general formula I,

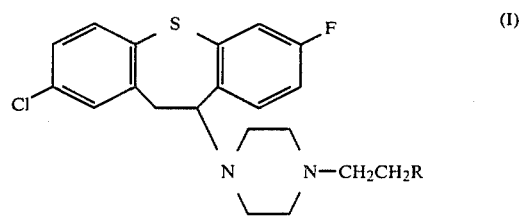

in which R represents an aminocarbonyl, aminooximinomethyl, 1,3-dioxolan-2-yl or 1,3-dioxan-2-yl, group and their addition salts with convenient organic and inorganic acids. These compounds are highly potent antidopaminergic, non-cataleptic neuroleptics of use in the treatment of schizophrenia. According to recent pharmacological assay results, the subject compounds are expected to be substantially free of the usual undesired extrapyramidal side effects. They can be obtained by common preparative methods from the respective starting compounds of formula III, IV or V, or also by appropriate interconversion reactions of other compounds of formula I. If required, the resulting bases are neutralized with suitable acids, preferably methanesulfonic, maleic or hydrochloric acid, to yield the corresponding addition salts that can be used in formulating proper dosage forms for pharmacological evaluation and therapeutical application.

6 Claims, No Drawings

N-SUBSTITUTED 2-CHLORO-7-FLUORO-10-PIPERAZINO-10,11-DIHYDRODIBENZO (B,F) THIEPINS AND ACID ADDITION SALTS THEREOF

BACKGROUND OF THE INVENTION

The invention concerns N-substituted 2-chloro-7-fluoro-10-piperazino-10, 11-dihydrodibenzo (b,f) thiepins of the general formula I

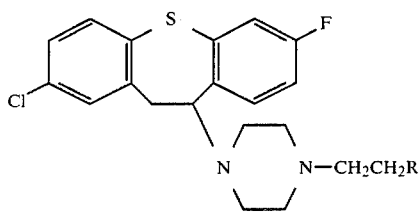

in which R represents an aminocarbonyl, aminooximinomethyl (amidoxime), 1,3-dioxolan-2-yl or 1,3-dioxan-2-yl group, and their addition salts with pharmaceutically acceptable organic and inorganic acids.

The compounds of the invention are highly potent antidopaminergic, non-cataleptic neuroleptic agents useful for the treatment of schizophrenia. According to recent pharmacological assay results, the compounds are surprisingly of low-toxicity and are expected to be substantially free of the common undesired extrapyramidal side effects (i.e. lowered motor coordination and related disturbances). Their acid addition salts, e.g. hydrochlorides, maleates and especially methanesulfonates, can be used in the formulation of dosage forms for pharmacological evaluation and therapeutic application.

The basic 10,11-dihydrodibenzo (b, f) thiepin skeleton of the compounds of formula I is a well-known carrier system for a number of neuroleptic substances from which several have found practical use in pharmacotherapy of schizophrenia, e.g. clorotepin (8-chloro-10-(4-methylpiperazino)-10,11-dihydrodibenzo (b,f) thiepin, Metysova J. et al, Acta Biol. Med. Ger. 39, 723, 1980), oxyprothepin (8-methylthio-10-(4-(3-hydroxypropyl) piperazino)-10, 11-dihydrodibenzo (b,f)-thiepin, Taussigova D. et al, Activ. Nerv. Supper. 16, 163, 1974), oxyprothepin decanoate (8-methylthio-10-(4-(3-decanoyloxypropyl)-piperazino)-10,11-dihydrodibenzo (b,f) thiepin, Zapletalek M. et al, Activ. Nerv. Super. 21, 138, 1979) and zotepin (2-chloro-11-(2-dimethylaminoethoxy)dibenzo (b,f) thiepin, Uchida S et al, Arzneim.-Forsch. 29, 1588, 1979).

Common disadvantages of all these compounds are their cataleptic action in rats and the corresponding extrapyramidal side effects in patients. The typical structural feature of the compounds of formula I, which evidently modifies their pharmacological profile in the desired direction, is the N-substituent —$CH_2CH_2R$ on the piperazine $N^4$. The relevant literature (Jilek J. O. et al, Collect. Czech. Chem. Commun. 36, 2226, 1971; 39, 3153, 1974; Rajsner M. et al, ibid. 42, 3079, 1977) describes only several compounds of the general formula II

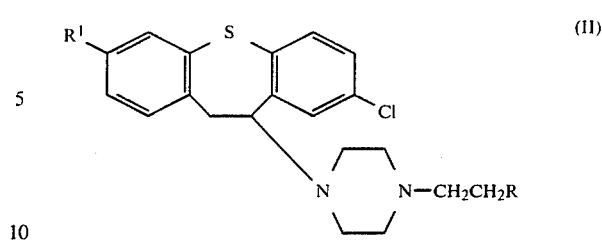

wherein R has the same meansing as in formula I and $R^1$ is a hydrogen or a fluorine atom. All these compounds, some of which differ from those of formula I merely by the position of the chlorine and fluorine atoms on the tricyclic skeleton, are also very potent neuroleptic agents, but simultaneously cause a significant cataleptic activity and, consequently, elicit extrapyramidal side effects in patients. One can only conclude that the noncataleptic character of the compounds of formula I, together with their high antidopaminergic activity in biochemical and pharmacological tests (cf. Sayed Y. and garrison J. M., Psychopharmacol. Bull. 19 (2), 283-288, 1983, "The dopamine hypothesis of schizophrenia and the antagonistic action of neuroleptic drugs—a review"), results from the specific location of the halogen (i.e. chlorine and fluorine) atoms on the skeleton, in combination with the particular structure of the piperazine $N^4$ substituent.

SUMMARY OF THE INVENTION

It is, therefore, an object according to the present invention to find new tricyclic compounds that do not provoke such undesirable side effects.

A typical and most interesting compound of the present invention has the structure 3-(4-(2-chloro-7-fluoro-10,11-dihydrodibenzo (b,f) thiepin-10-yl) piperazino) propionamide, which was pharmacologically tested as the methanesulfonate (compound A). This compound was tested using oral administration, and the numerical data given were calculated per base. Acute toxicity was evaluated in mice, and the result, obtained in 48 h, is considered representative: $LD_{50}=336$ mg/kg in male mice and 316 mg/kg in female mice. Longer evaluation of the toxicity test leads to lower $LD_{50}$ values, which is not the result of toxicity of the compounds, but rather a deep central depression of the animals which perish due to insufficient feed and water intake. For comparison, the value of acute toxicity of clozapine, i.e. 8-chloro-11-(4-methylpiperazine)-5H-dibenzo (b,e)-(1,4)diazepine (Lindt S. et al, Farmaco, Ed. Prat. 26, 585, 1971) is $LD_{50}=199$ mg/kg. The acute toxicity of compound A in male rats is $LD_{50}=654$ mg/kg. In the test of inhibition of spontaneous locomotor activity in mice, the medium active dose of compound A, $D_{50}=1.05$ mg/kg (clozapine is approx. 4 times less active; chlorpromazine is 5 times less active and haloperidol is approx. twice as active). Results in this test correspond to the central depressant, i.e. sedative, activity of the compounds. In the rota-rod test in mice, the disturbances of the motor coordination are evaluated: the medium effective dose $ED_{50}=2.0$ mg/kg; the same in rats, $ED_{50}=19.5$ mg/kg. At the dose of 50 mg/kg, the compound A lacks cataleptic activity in rats (clozapine behaves similarly). In the test of antiapomorphine action in rats, compound 1 at doses of 20 and 50 mg/kg, by 2 h after the administration, significantly inhibits the agitation, but does not affect the apomorphine-elicited stereotypes (clozapine at the same doses effects neither agitation nor stereotypes). In the test of inhibition of apomorphine emesis in dogs, the threshold activity dose of compound A is 2 mg/kg by 4 h after the administration (within 24 h the effect disappears). In the test of apomorphine-induced climbing behavior of mice, the medium effective dose of compound A is $PD_{50}=2.9$ mg/kg (chlorpromazine has approx. 50%, and clozapine 20% of this activity; haloperidol is more active). In the interval of 3 h after the administration, compound A intensively increases the level of homovanillic acid (as the main dopamine metabolite) in corpus striatum and tuberculum olfactorium of the rat brain. Threshold doses which significantly increase the homovanillic acid concentration of 5 mg/kg for corpus striatum, and 2 mg/kg for tuberculum olfactorium. This test is the most important criterion of the antidopaminergic activity of the compounds; clozapine has about 1/10 of the activity in both mentioned brain structures. Moreover, compound A at a dose of 20 mg/kg does not significantly affect the dopamine levels in either of the structures (clozapine slightly decreases dopamine levels). For checking the affinity of compound A to dopamine receptors in the two brain structures, the inhibition of 0.5 nM $^3$H-spiperone, i.e. 8-(4-(4-fluorophenyl)-4-oxobutyl)-1-phenyl-1,3,8-triazaspiro (4,5) decan-4-one binding is evaluated. The inhibitory concentration of compound A is $IC_{50}=49.74$ nM for corpus striatum and 30.56 nM for tuberculum olfactorium. Clozapine in the same test is approx. 5 times weaker, and haloperidol 4 to 5 times more active. In conclusion, the tests performed prove that compound A is noncataleptic and has 5 to 10 times higher antidopaminergic activity than clozapine.

A further compound of the invention is 1-(2-chloro-7-fluoro-10, 11-dihydrodibenzo (b,f) thiepin-10-yl)-4-(2-(1,3-dioxolan-2-yl)ethyl)piperazine, which also was tested as the methanesulfonate (compound B). This compound and the following ones were likewise administered orally, and the data is calculated per bases. Acute toxicity in mice is $LD_{50}=350$ mg/kg. Discoordinating effect in the rota-rod test in mice is $ED_{50}=3.5$ mg/kg. At the dose of 50 mg/kg, it has no cataleptic effect in rats, and at the same dose it only mildly potentiates the cataleptogenic effect of perphenazine. At the same dose, there is only a slight indication of antiapomorphine effect in rats. At the dose of 80 mg/kg, after an interval of 3 h, it increases the homovanillic acid level in the rat brain striatum by 504%; simultaneously it lowers the dopamine level by 25%.

The invention further includes 1-(2-chloro-7-fluoro-10, 11-dihydrodibenzo (b,f) thiepin-10-yl)-4-(2-(1,3-dioxan-2-yl) ethyl)piperazine, which is also tested as the methanesulfonate (compound C). Acute toxicity in mice, i.e. $LD_{50}$ is higher than 500 mg/kg; on intravenous administration, $LD_{50}=77.6$ mg/kg. Discoordinating activity in the rota-rod test in mice turns out to be $ED_{50}=2.86$ mg/kg. At the dose of 50 mg/kg, compound C has no cataleptic effect and only mildly potentiates the cataleptogenic effect of perphenazine in rats. At the same dose, it does not reveal any antiapomorphine effect in rats. At the dose of 20 mg/kg (3 h interval) it increases the homovanillic acid level in the rat striatum by 400% (clozapine at the same dose, by 200%); the dopamine level is not affected. The affinity of compound C to dopamine receptors in striatum on the basis of release of $^3$H spiperone is approximately the same as with clozapine.

Finally, 3-(4-(2-chloro-7-fluoro-10,11-dihydrodibenzo (b,f)-thiepin-10-yl) piperazino)propionamidoxime, which is also included within the scope of the invention, is tested in the form of the dimaleate (compound D). Acute toxicity in mice is $LD_{50}=320$ mg/kg. In the test of affecting the motility of mice according to Ther, the medium effective dose of compound D is 50 mg/kg. At the dose of 80 mg/kg (3 h after the administration) this compound increases homovanillic acid level in rat striatum by more than 300%; the increase is significant already after a dose of 20 mg/kg. The reported results indicate that compounds B, C, and D are approximately comparable with regard to their pharmacological profiles to the aforementioned compound A.

The subject compounds of formula I of the present invention are available by common reactions from intermediary compounds of formulas III, IV, or V

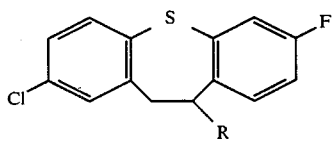

(III, R = Cl)

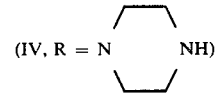

(IV, R = N⟨⟩NH)

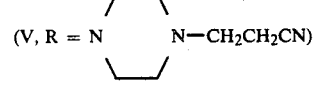

(V, R = N⟨⟩N—CH$_2$CH$_2$CN)

(for their preparation, cf. Jilek J. O. et al. Collect. Czech. Chem. Commun. 40, 2887, 1975) or by interconversion of other compounds of formula I.

Compound A of formula I, wherein R is an aminocarbonyl group, can be prepared best from compound IV by its addition reaction with acrylamide. This reaction can be conducted under various conditions, preferably by the procedure of Example 1, infra in tert-butanol at a temperature of 50°–55° C., in the presence of benzyltrimethyl-ammonium hydroxide and a small amount of sulfur. This procedure affords the crystalline compound A in yields of approx. 90% of theory. The product crystallizes from ethanol in two modifications: a more stable one, melting at 183°–184° C., and a less stable one, having a lower m.p. of 154°–155° C. Neutralization of compound A base with maleic and methanesulfonic acids gives, respectively, neutral maleate, m.p. 124°–128° C., poorly soluble in water, and monomethanesulfonate, m.p. 172°–173° C., excellently water-soluble.

Compound A can also be prepared by a substitution reaction of compound III with 3-(1-piperazinyl)propionamide (obtained according to U.S. Pat. No. 3,352,866), preferably by refluxing the reaction mixture containing a 100–150% excess of the latter reactant with a small amount of chloroform; the crystalline base is obtained in a yield of approx. 60% of theory. Concurrent dehydrochlorination reaction gives a certain amount of neutral 2-chloro-7-fluorodibenzo (b, f) thiepin, m.p. 98° C.

Compound B of formula I, wherein R is a 1,3-dioxolan-2-yl, can be prepared by substitution reaction of compound IV with 2-(2-chloroethyl)-1,3-dioxolane (obtained according to Ratouis R., Roissier J. R., Bull. Soc. Chim. France 1966, 2963), preferably in boiling toluene, in the presence of triethylamine for binding the formed hydrogen chloride. The resulting non-homogeneous reaction product is purified by column chromatography on aluminium oxide; the purified crystalline base, melting at 112°–114° C., is obtained in a yield of over 50% of theory. Its neutral maleate, m.p. 166°–168° C., is slightly soluble in water, whereas its monomethanesulfonate, melting at 158°–159° C., is readily water-soluble.

Compound C of formula I, wherein R is 1,3-dioxan-2-yl, is prepared by a quite similar substitution reaction of compound IV with 2-(2-chloroethyl)-1,3-dioxane (Ratouis R., Boissier J. R., l.c.). In this case, the chromatographic purification of the crude base is not necessary, and the crystalline base, melting at 150.5°–152.5° C., is obtained in a yield of approx. 65% of theory. Neutral maleate, m.p. 184°–185° C. is poorly soluble in water, and monomethanesulfonate, m.p. 202°–204° C., is again excellently water-soluble.

Compound D of formula I, wherein R is an aminooximinomethyl group $C(NH_2)=NOH$, is prepared by reacting the corresponding nitrile V with hydroxylamine in boiling methanol. The so-obtained crude base in neutralized with maleic acid, to give crystalline dimaleate, which crystallizes as a hemihydrate melting at 159°–163° C. (ethanol-ether).

The identity of all compounds of the invention referred to herein has been verified both analytically and spectrographically.

Acid addition salts of the products, insofar as they are moderately water-soluble, are convenient for the formulation of solid oral dosage forms (i.e. tablets, coated tablets, capsules), whereas those salts that are readily soluble in water can also be formulated into liquid dosage forms, either oral (drops) or parenteral (injection solutions).

Further particulars of the preparative procedures are illustrated by the subsequent non-limitative examples.

DESCRIPTION OF THE PREFERRED EMBODIMENTS

EXAMPLE 1

3-(4-(2-Chloro-7-fluoro-10,11-dihydrodibenzo(b,f) thiepin-10-yl)piperazino)propionamide (formula I, R is $CONH_2$)

A mixture of tert-butanol (400 ml), 2-chloro-7-fluoro-10-piperazino-10,11-dihydrodibenzo(b,f)thiepin (40.0 g), elemental sulfur (0.45 g), 40% methanolic benzyltrimethylammonium hydroxide solution (4 ml) and acrylamide (36.5 g) is stirred for 15 hours in a water bath at 50°–55° C. At first, the reaction mixture is heterogeneous, but after approx. 8 hours of stirring and warming it forms a clear yellow solution. When the reaction is completed, the solution is allowed to stand at room temperature overnight in order to crystalline. The product is collected on a filter and washed successively with small amounts of tert-butanol, toluene and hexane, and then dried to constant weight. The obtained first-crop material (35.4 g, 74% of theory) melts at 172°–178° C.

Mother liquors are evaporated under reduced pressure from a water bath maintained at 70°–80° C. The residue (43.5 g) is shaken at 30°–35° C. with a two-phase system consisting of toluene (350 ml) and water (400 ml), the organic phase is washed with warm water (3×250 ml), the toluene solution is filtered and the product is extracted from the filtrate with a solution of methanesulfonic acid (10 g) in water (100 ml), and finally, with water (60 ml). The combined aqueous solutions are filtered with active carbon (4 g), the filtrate is made alkaline by the addition of aqueous ammonia (30 ml) and the separated second-crop product is taken into chloroform. The organic layer is washed with warm water (80 ml), dried over anhydrous potassium carbonate, filtered and evaporated under reduced pressure to dryness. The residue is dissolved in hot toluene (22 ml), and the solution is allowed to crystallize at room temperature. After standing overnight, the product is separated, washed successively with small amounts of toluene and hexane, and dried in vacuo to give the purified second-crop material (10.1 g, 21% of theory) melting at 174°–175° C. The total yield is 45.5 g (95%).

The pure base is obtained by chromatography of a sample of the product on a column packed with aluminium oxide (neutral, activity II). Elution of the column with benzene removes a minor quantity of the material formed by less polar impurities, and a mixture of benzene with 5% of ethanol then washes out the chromatographically uniform desired base (3.7 g), which can be purified by crystallization from a mixture of boiling ethanol (10 ml) and petroleum ether (10 ml). Another crystallization from ethanol alone affords a more stable, higher-melting crystal modification, having a m.p. of 183°–184° C. Its elemental analysis corresponds to the summary formula $C_{21}H_{23}ClFN_3OS$. It seldom happens that the chromatographic purification of a sample and subsequent crystallization of the resulting homogeneous base yields the corresponding less stable, lower-melting modification with a m.p. of 154°–155° C. (ethanol). Both these modifications have identical $^1H$ NMR spectra (in $C_2HCl_3$), whereas their IR absorption spectra in nujol show minor differences.

The crude product melting at 172°–178° C. may sometimes contain certain amounts of the starting base; this can be checked by thin-layer chromatography on silica gel. In such a case, the following purification procedure is recommended: The crude base (34.5 g) is suspended in a solution of methanesulfonic acid (10 g) in water (500 ml). By moderate warming of the suspension to approx. 50° C., the bases are converted into soluble methanesulfonates and a clear solution is formed. The obtained yellow solution is filtered while hot with active carbon (10 g), the filtrate is made alkaline under stirring by slow addition of aqueous ammonia (35 ml), toluene (70 ml) is then added, and the mixture is stirred for another hour and then allowed to stand at room temperature for 12 hours. The separated crystalline product is collected on a filter, successively washed with water (50 ml), toluene (20 ml) and hexane (20 ml), and then dried in vacuo to give the purified base (31.8 g) melting at 175°–179° C. The purification effect of this procedure results from the fact that the unreacted starting base remains dissolved in toluene added after making the solution of methanesulfonates alkaline with aqueous ammonia.

If the corresponding pure methanesulfonate is required, the obtained base (10.0 g) and methanesulfonic acid (2.28 g) are dissolved in ethanol (50 ml), the solution is filtered, the filtrate is diluted with hexane (50 ml) and then the mixture is allowed to stand at room temperature for 12 hours to crystallize. Crystals are separated, washed with an ethanol-hexane mixture, and then dried in vacuo. The yield is 10.3 g (84%) of the methanesulfonate salt melting at 171°–172° C. Crystallization from ethanol-ether give an analytical sample having a m.p. of 172°–173° C.; its composition corresponds to the summary formula $C_{22}H_{27}ClFN_3O_4S_2$.

Neutralization of the base (15.1 g) dissolved in hot ethanol (170 ml) by adding a solution of maleic acid (4.2 g) in ethanol (15 ml) provides the neutral maleate (13.2 g), which can be purified by crystallization from ethanol to a constant m.p. of 124°–128° C., and has the composition $C_{22}H_{27}ClFN_3O_5S$.

EXAMPLE 2

3-(4-(2-Chloro-7-fluoro-10,11-dihydrodibenzo (b,f) thiepin-10-yl)piperazino)propionamide (I, R=$CONH_2$)

A mixture of 2,10-dichloro-7-fluoro-10,11-dihydrodibenzo(b,f)-thiepin (2.8 g), 3-(1-piperazinyl)propionamide (3.2 g) and chloroform (10 ml) is refluxed with stirring for 8 hours. The solvent is than evaporated under reduced pressure, and the residue is extracted by shaking with a two-phase system consisting of benzene (30 ml) and a solution of methanesulfonic acid (4 g) in water (50 ml). The clear aqueous solution is separated and then made alkaline with aqueous ammonia (10 ml). The so-formed suspension of the amorphous base is diluted with ethanol (100 ml), and the mixture is briefly warmed to boiling. The resultant clear solution is then allowed to crystallize at room temperature for 6 hours. The crystalline product is separated, washed with a small amount of ethanol, and then dried in vacuo. The obtained base (2.35 g, 60% of theory) melts at 179°–182° C.; it can be purified by crystallization from ethanol to give the title compound having a m.p. of 182°–184° C. and which is identical with the product of the preceding example 1.

EXAMPLE 3

1-(2-Chloro-7-fluoro-10,11-dihydrodibenzo(b,f)thiepin-10-yl)-4-(2-(1,3-dioxolan-2-yl) ethyl)piperazine (I, R=1,3-dioxolan-2-yl)

A mixture of 2-chloro-7-fluoro-10-piperazino-10,11-dihydro-dibenzo(b,f)thiepin (10.9 g), toluene (70 ml), triethylamine (10.9 g) and 2-(2-chloroethyl)-1, 3-dioxolane (16.5 g) is refluxed under stirring for 24 hours. After cooling, the precipitate is filtered off, the filtrate is washed with water, dried over anhydrous potassium carbonate, filtered with active carbon, and then the filtrate is evaporated under reduced pressure. The obtained non-homogeneous residue (17.6 g) is dissolved in benzene and chromatographed on a column packed with neutral aluminium oxide (activity II, 400 g). By elution of the column with benzene, some non-crystallizing material (5.9 g) is first washed out, followed by the desired crystalline base (7.6 g, 54% of theory) melting at 110°–114° C. Subsequent crystallization from benzene provides the pure base, which melts at 112°–114° C.; its elemental analysis corresponds to the presumed composition $C_{23}H_{26}ClFN_2O_2S$. Neutralization of the base with maleic acid in ethanol gives the neutral maleate $C_{27}H_{30}ClFN_2O_6S$; after crystallization from ethanol, the pure substance melts at 166°–168° C. The product is slightly soluble in water. Neutralization of another sample of the above base with methanesulfonic acid in ethanol, and subsequent addition of ether, yields the monomethanesulfonate $C_{24}H_{30}ClFN_2O_5S_2$, which, after crystallization from an ethanol—ether mixture, melts at 158°–159° C. This salt is excellently water-soluble: it provides better than 10% aqueous solutions.

EXAMPLE 4

1-(2-Chloro-7-fluoro-10,11-dihydrodibenzo(b,f)thiepin-10-yl)-4-(2-(1,3-dioxan-2-yl)ethyl)piperazine (I, R=1, 3-dioxan-2-yl)

A mixture of 2-chloro-7-fluoro-10-piperazino-10,11-dihydro-dibenzo(b,f)thiepin (10.0 g), toluene (60 ml), triethylamine (10 g) and 2-(2-chloroethyl)-1,3-dioxane (15.3 g) is refluxed under stirring for 23 hours. On cooling, the precipitate is filtered off and washed with benzene. The combined filtrates are then washed with water, dried over anhydrous potassium carbonate, filtered with a small amount of active carbon, and evaporated under reduced pressure to dryness. The residue (19.0 g) crystallizes rapidly while standing. Another crystallization from a mixture of benzene (50 ml) and petroleum ether (50 ml) yields 8.5 g (65%) of the desired base, melting at 150.5°–152° C. Repeating the crystallization from the same solvent system does not increase the m.p. any more; the product is analytically pure, and its elemental analysis corresponds to the composition $C_{24}H_{28}ClFN_2O_2S$. Neutralization of the base, with maleic acid in a mixture of equal amounts of benzene, acetone and ethanol, provides the neutral maleate $C_{28}H_{32}ClFN_2O_6S$, which crystallizes from ethanol and melts in the pure state at 184°–185° C. This salt is only very slightly soluble in water. Neutralization of base with methanesulfonic acid in ethanol gives the monomethanesulfonate $C_{25}H_{32}ClFN_2O_5S_2$, which crystallizes from ethanol and melts at 201°–203° C. This salt is excellently water-soluble.

EXAMPLE 5

3-(4-(2-Chloro-7-fluoro-10,11-dihydrodibenzo(b,f) thiepin-10-yl)piperazino) propionamidoxime (I. R is $C(NH_2)=NOH$)

A sodium methoxide solution, prepared by dissolving sodium metal (0.25 g) in methanol (6 ml), is treated with hydroxylamine hydrochloride (0.74 g). After a brief stirring, 3-(4-(2-chloro-7-fluoro-10,11-dihydrodibenzo(b,f)thiepin-10-yl) piperazino) propionitrile (3.54 g) is added. The mixture is refluxed for 7.5 hours, filtered on cooling, and then the filtrate is evaporated under reduced pressure to give 4.0 g (approx. the theoretical amount) of the non-crystalline base. Neutralization of a portion (3.1 g) of the crude material with maleic acid (2.5 g) in ethanol (30 ml) gives the dimaleate (2.5 g), which can be purified by crystallization from a mixture of 96% ethanol and ether to give the pure salt hemihydrate $C_{29}H_{32}ClFN_4O_9S.0.5H_2O$, melting at 161°–163° C.

The starting nitrile, which has been described in the literature merely as its maleate, can easily be prepared in the form of they crystalline base, m.p. 97°–99° C. (ethanol). This base is used as the starting material for the above described preparation.

Although the invention is described and illustrated with reference to a plurality of embodiments thereof, it is to be expressly understood that it is in no way limited to the disclosure of such preferred embodiments but is capable of numerous modifications within the scope of the appended claims.

We claim:

1. N-substituted 2-chloro-7-fluoro-10-piperazino-10,11-dihydrodibenzo(b,f)thiepin of the formula

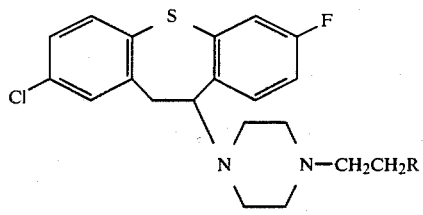

in which R is selected from the group consisting of an aminocarbonyl, amino-oximinomethyl, 1,3-dioxolan-2-yl and 1,3-dioxan-2-yl group, and its addition salt with a pharmaceutically acceptable organic or inorganic acid.

2. 3-(4-(2-Chloro-7-fluoro-10,11-dihydrodibenzo(b,f)thiepin-10-yl)piperazino)propionamide, its maleate and its methanesulfonate.

3. 3-(4-(2-Chloro-7-fluoro-10,11-dihydrodibenzo(b,f)thiepin-10-yl)piperazino)propionamidoxime, its maleate and its methanesulfonate.

4. 1-(2-Chloro-7-fluoro-10,11-dihydrodibenzo(b,f)thiepin-10-yl)-4-(2-(1,3-dioxolan-2-yl)ethyl)piperazine, its maleate and its methanesulfonate.

5. 1-(2-Chloro-7-fluoro-10,11-dihydrodibenzo(b,f)thiepin-10-yl)-4-(2-(1,3-dioxan-2-yl)ethyl)piperazine, its maleate and its methanesulfonate.

6. Composition useful for the treatment of schizophrenia in humans comprising an antidopaminergic and neuroleptic effective amount of an N-substituted 2-chloro-7-fluoro-10-piperazino-10,11-dihydrodibenzo(b,f)thiepin of the formula

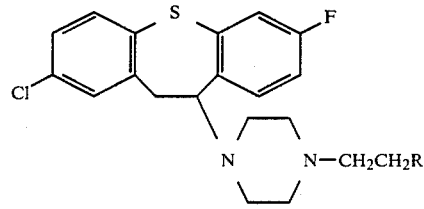

in which R is selected from the group consisting of an aminocarbonyl, amino-oximinomethyl, 1,3-dioxolan-2-yl and 1,3-dioxan-2-yl group, and its addition salt with a pharmaceutically acceptable organic or inorganic acid, in a pharmaceutically acceptable carrier.

* * * * *